United States Patent [19]
van Holst et al.

[11] Patent Number: 5,587,312
[45] Date of Patent: Dec. 24, 1996

[54] SOMATIC EMBRYOGENESIS METHOD

[75] Inventors: Gerrit J. van Holst, Enkhuizen; Marc Kreuger, Bovenkarspel; Wiert van der Meer, Enkhuizen; Erik Postma, Hoorn; Rob Abbestee, Enkhuizen, all of Netherlands

[73] Assignee: Sandoz Ltd., Basel, Switzerland

[21] Appl. No.: 406,822

[22] Filed: Mar. 20, 1995

Related U.S. Application Data

[63] Continuation of Ser. No. 180,253, Jan. 12, 1994, abandoned.

[30] Foreign Application Priority Data

| Jan. 15, 1993 | [GB] | United Kingdom | 9300705 |
| Jan. 15, 1993 | [GB] | United Kingdom | 9300706 |
| Jan. 15, 1993 | [GB] | United Kingdom | 9300707 |
| Jan. 15, 1993 | [GB] | United Kingdom | 9300729 |

[51] Int. Cl.$^6$ .............................. C12N 5/00; C12N 5/02
[52] U.S. Cl. ................... 435/240.46; 435/240.4; 435/240.45
[58] Field of Search .................. 435/240.45, 240.46, 435/240.4

[56] References Cited

U.S. PATENT DOCUMENTS

| 5,024,944 | 6/1991 | Collins et al. | 435/172.3 |
| 5,030,572 | 7/1991 | Powo et al. | 435/240.5 |
| 5,236,841 | 8/1993 | Gupta | 435/240.45 |
| 5,294,594 | 3/1994 | Pullman et al. | 435/240.45 |
| 5,334,530 | 8/1994 | Woods et al. | 435/240.48 |
| 5,413,929 | 5/1995 | Ishizaki et al. | 435/240.46 |
| 5,482,857 | 1/1996 | Gupta et al. | 435/240.45 |
| 5,491,090 | 2/1996 | Handley, III et al. | 435/240.46 |

FOREIGN PATENT DOCUMENTS

WO91/13159  9/1991  WIPO.

OTHER PUBLICATIONS

Coutos-Thevenot, Pierre et al., "Embryogenic and non-embryogenic cell lines of *Daucus carota* cloned from meristematic cell clusters: relation with cell ploidy determined by flow cytometry," *Plant Cell Reports*, (1990) 8, 605–608.
de Vries, Sacco C. et al., "Acquisition of embryogenic potential in carrot cell-suspension cultures," Department of Molecular Biology, Agricultural University Wageningen, De Dreijen, NL and Department of Biology, Texas A&M University, Texas, USA., *Planta*, (1988) 176:196–204.
(Abstract only–85–183834/30) WO 85/03085–A, Jan. 16, 1984.
(Abstract only–93–060894/08) JP 05007438–A, Dec. 28, 1990.
(Abstract only–93–049106/06) JP 05000033–A, Dec. 26, 1990.
(Abstract only–93–006209/01) JP 04335838–A, May 9, 1991.
(Abstract only–92–418057/51) JP 04311326–A, Dec. 26, 1990.
(Abstract only–92–418058/51) JP 04311327–A, Dec. 26, 1990.
(Abstract only–91–364957/50) JP 03244328–A, Feb. 23, 1990.
(Abstract only–91–033480/05) JP 02303432–A, May 17, 1989.
(Abstract only–90–373645/50) JP 90053007–B, Nov. 15, 1990.
(Abstract only–90–245127) JP 02245127–A, Sep. 28, 1990.
(Abstract only–93–190691/24) JP 05115280–A, Apr. 30, 1991.
(Abstract only–93–190655/24) JP 05115228–A, Apr. 9, 1991.
(Abstract only–92–190228/23) JP 92026804–B, Mar. 14, 1989.
(Abstract only–92–418059/51) JP 04311328–A, Apr. 8, 1991.
(Abstract only–92–409733/50) JP 04304824–A, Mar. 29, 1991.
(Abstract only–92–418097/51) JP 04311384–A, Apr. 11, 1991.
(Abstract only–93–006208/01) JP 04335837–A, May 8, 1991.
(Abstract only–90–144845/19) JP 02092221–A, Sep. 30, 1988.
(Abstract only–88–305125/43) JP 63226215–A, Mar. 16, 1987.
(Abstract only–93–131183/16) JP 05070316–A, Sep. 10, 1991.
(Abstract only–93–111782/14) JP 05049359–A, Jul. 26, 1991.
(Abstract only–93–006210/01) JP 04335839–A, May 9, 1991.
(Abstract only–92–334384/41) HU 60325–T, Oct. 25, 19990.
(Abstract only–92–248249/30) SU 1685323–A1, May 4, 1989.
(Abstract only–92–232965/28) SU 1683583–A1, Mar. 28, 1989.
J. Evans, D. A. et al, *Handbook of Plant Cell Culture*, vol. 1, chap. 3, p. 82–123, 1983, Macmillan Publishing Co., New York, N.Y.

*Primary Examiner*—Michael G. Wityshyn
*Assistant Examiner*—Kristin K. Larson
*Attorney, Agent, or Firm*—Lynn Marcus-Wyner

[57] ABSTRACT

Somatic embryo suspension cultures and pro-embryogenic mass suspension cultures (PEMs) comprising somatic embryos and PEMs having substantially similar ploidy levels, plants derived therefrom, and methods for obtaining said somatic embryos.

14 Claims, 1 Drawing Sheet

SOMATIC EMBRYOGENESIS METHOD

This application is a continuation application of application Ser. No. 08/180,253, filed Jan. 12, 1994, now abandoned.

The present invention relates to improved somatic embryogenesis methods suitable for regenerating whole plants from tissue culture and more specifically to improved methods for the obtention of somatic embryos via somatic embryogenesis using liquid media per se.

BACKGROUND

Commercialization of a process making effective use of somatic embryogenesis is considered desirable over and economically more attractive than, for example, organogenic cloning because of the potential for higher yields of plants over comparatively short time intervals.

It is known that certain plant cells have the potential to differentiate into whole plants when cultured in appropriate plant tissue culture media. Such media typically comprise inorganic salts, a carbon source such as sucrose, inositol, thiamine, and the like. Examples of plant tissue culture media commonly used are those of Murashige and Skoog (MS medium), Lindsmaier and Skoog, Gamborg (B5 medium), and the like.

The composition of such plant tissue culture media may be modified to optimize the growth of the particular plant cells employed. Almost all plant cells require plant hormones e.g. auxins or auxin-like compounds such as indole acetic acid, indole butyric acid, naphthalene acetic acid, or 2,4-D, and/or a cytokinin such as benzyl adenine, zeatin, kinetin, or the like. In order to secure optimal growth it may also be advantageous to add vitamins such as nicotinic acid, pyridoxine or other components such as coconut milk, caseine hydrolyzates and the like.

In the past, the formation of true somatic embryos has required the use of callus material which comprises undifferentiated conglomerates of cells having very large vacuoles and smaller, round cells having very small vacuoles, as the primary growth phase material from which somatic embryos can then be derived. However, the use of such material as starting material in somatic embryogenesis has many drawbacks and has proven to be of limited use in the obtention of large numbers of plants having substantially similar phenotype and/or being substantially uniform with respect to ploidy level. Plants originating from callus have a tendency to display somaclonal variation and/or non-uniformity with respect to ploidy level [(Chaleff R. S. (1983) Science 219:676–682; Larkin P. J. (1987) Iowa State Journal of Research 61(4):393–434; De Klerk G-J (1990) Acta Bot. Neerl.39(2):129–144; Karp A. & Bright S. W. J. (1985) Oxford Surveys of Plant Molecular & Cell Biology 2:199–234; Custers J. B. M. et al (1990) Acta Bot. Neerl. 39(2):153–161 (cucumis sativus L.); Kysely W. et al (1987) Plant cell Reports 6:305–308 (pisum sativum L.); Ezura H. (1992) Plant Science 85:209–213 (cucumis melo); and Kiviharju E. et al (1992) Plant Cell, Tissue, and Organ Culture 28:187–194 (Cyclamen persicum Mill)].

Known examples of patent applications make use of callus material in somatic embryogenesis. An example, WO90/01058 to Plant Genetics Inc. describes using callus material to acquire somatic embryos while investigating the effect of employing a wide range of synthetic auxins. Callus material is formed or grown from suitable explant material over many weeks of culturing and/or subculturing on solid media. Somatic embryogenesis is then initiated by transferring callus tissue to a medium containing a plant hormone such as 2,4-D or an analogue thereof. No mention is made of the ploidy level of somatic embryos, or of the ploidy level of plants obtained. While the use of callus material in somatic embryogenesis may be helpful in obtaining plants in which the obtention of somaclonal variants may be interesting for enriching an available gene pool, it is of little use for seed merchants or breeders who simply wish to obtain commercial numbers of plants which have substantially all the same genotype.

It is acknowledged that carrot cell lines have been cloned from microclusters composed of meristematic cells and studied for their capacity to produce embryos. (P. Coutos-Thevenot et al, Plant Cell Reports (1990) 8: 605–608).

The authors report employing an initial cell suspension from hypocotyls of domestic carrot (S1 strains) in a plant tissue culture medium comprising the auxin 2,4-D, isolating cell clusters by filtration, resuspending the cell clusters in plant tissue culture medium comprising 2,4-D to increase the cluster population density, transferring cell colonies from isolated clusters to a Petri dish comprising solid plant tissue culture medium containing 2,4-D and 1% bacto-agar to induce cell colony formation and depositing them in a 2nd solid medium containing 2,4-D and 1% bacto-agar around a nurse S1 strain callus, dissociating each cell colony in plant tissue culture medium containing 2,4-D and subculturing the thus obtained cultures in plant tissue culture medium containing 2,4-D. The subsequent analysis of the cell lines obtained according to this process revealed that 13 out of 40 cell lines were embryogenic, but most of these lines lost their embryogenic potential over time. Only one cell line had a rather constant embryogenic potential over a larger period. According to flow cytometric analysis the latter line was diploid.

The present invention provides a method of obtaining somatic embryos in suspension culture which is technically simple. It does i.a. not require the deposition of cell lines around a nurse callus. The method of the invention allows accordingly the production of somatic embryos at a commercial scale. The somatic embryos according to the invention, are capable of being used to provide commercial quantities of plants having substantially the same genotype.

Hitherto, somatic embryogenesis has been indicated as a potentially powerful tool in the obtention of plants, however, the impracticalities of utilizing somatic embryogenesis starting from callus material have prevented the successful exploitation of the technology.

It has now surprisingly been found that commercial quantities of true somatic embryos can be obtained through the employment of liquid culturing techniques per se and without the need to employ solid media and/or callus tissue. It has also been found that it is possible to increase the biomass of PEMs in liquid media and hence a capacity to produce somatic embryos in commercial quantities therefrom. Using such liquid culturing techniques obviates the need to employ callus culturing/callus sub-culturing steps and provides for the first time a means of obtaining populations of somatic embryos which are uniform with respect to ploidy level.

The present invention provides a method for obtaining somatic embryos via somatic embryogenesis which substantially reduces or eliminates the risk of obtaining somaclonal variants.

It provides non-Daucus somatic embryo suspension cultures wherein the ploidy level of somatic embryos contained therein is substantially uniform.

The invention further provides plants having a substantially uniform ploidy (e.g. diploid plants or tetraploid plants) derived from somatic embryo suspension cultures having substantially the desired ploidy level.

The invention provides a more reliable means of obtaining true somatic embryos in commercial quantities from explant material which does not rely on the employment of callus tissue and/or employ solid media as essential elements of the said means.

These and other objects of the invention will become apparent from a reading of the following description and examples.

DETAILED DESCRIPTION

Figure 1:
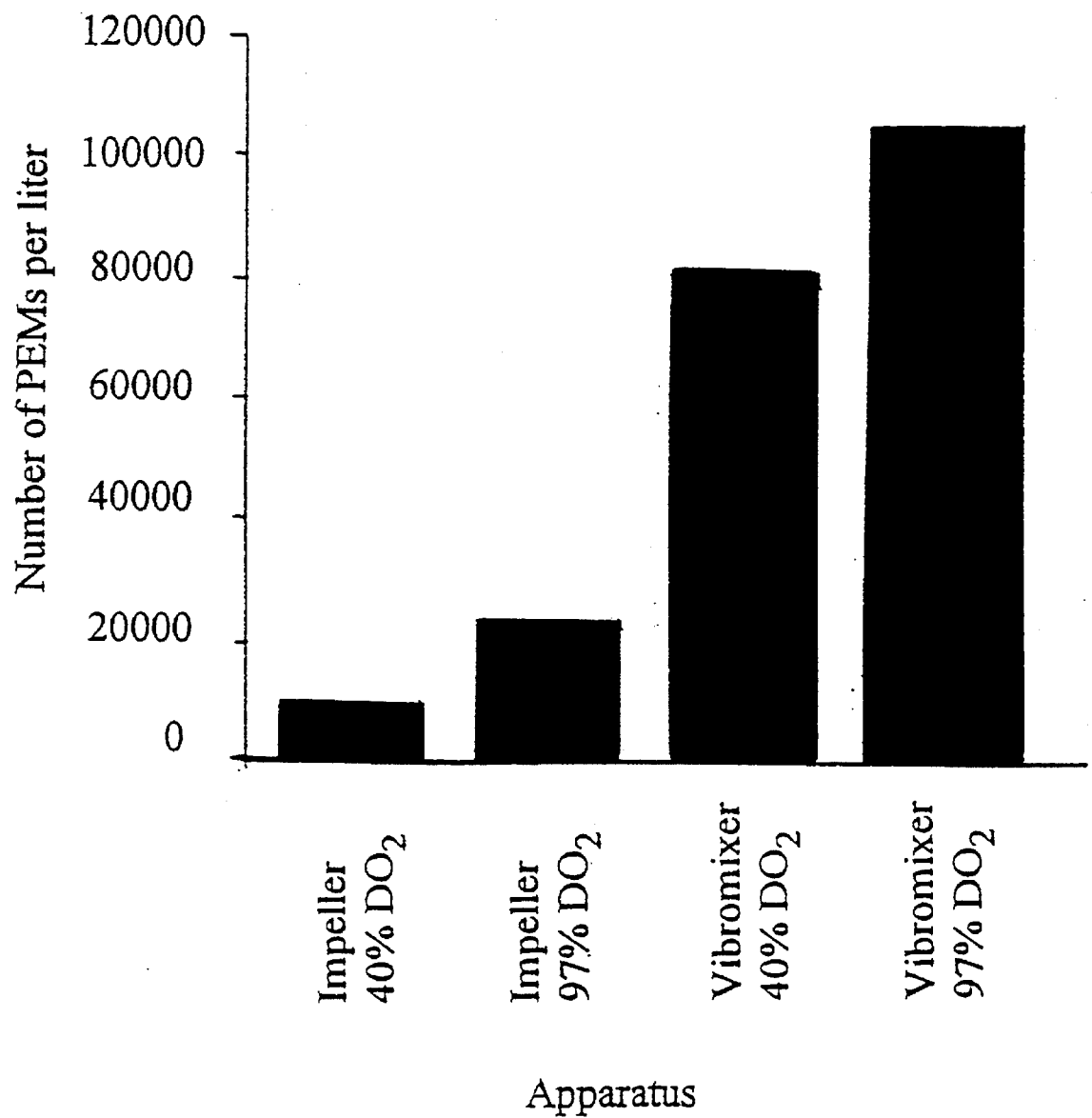
FIG. 1 shows a comparison between the number of PEMs obtained per liter when an impeller is used and when a vibromixer is used.

The invention provides a method of promoting pro-embryogenic mass (PEM) formation from explant material wherein the PEMs are capable of giving rise to viable, somatic embryos characterized in that non-callus plant tissue is placed in contact with a liquid plant tissue culture medium including an effective amount of an auxin or mixture of auxins.

Promoting pro-embryogenic mass (PEM) formation means that PEM formation can be induced and/or PEM biomass can be increased.

The explant material employed may be dicotyledonous or monocotyledonous plant species. Preferably, the explant material is derived from a dicotyledonous plant species. Typically, the somatic embryos are derived from proembryogenic masses (PEMs), structures which are morphologically distinct from callus material and are also known as meristematic clusters. The PEMs have the same ploidy level or ploidy levels as the explant material from which they are derived. Thus, where explant material comprising diploid and tetraploid cells is taken from a diploid plant, diploid and tetraploid PEMs resulting therefrom may have to be separated out via sieving, cell sorting or the like prior to further culturing in liquid medium.

PEMs comprise substantially differentiated growing plant tissue and can be regarded as precursors of true, somatic embryos. Under the light microscope (×40 to ×100 magnification) PEMs appear as conglomerates of small, round, cytoplasm rich cells comprising small vacuoles. As such the PEMs of the instant invention can be regarded as being substantially identical in genetic terms to the parent cells of plants from which they are derived and ultimately give rise to true somatic embryos which embryos are recognizable as being bipolar ie having the capability of giving rise to roots and shoots from meristematic root and shoot tissues. Thus, a viable true somatic embryo is also one which can give rise to at least one plantlet which is substantially identical, genetically speaking, to the explant progenitor cellular material from which it is derived, when subjected to appropriate further treatments as commonly employed in the art.

Plant tissue material suitable for use in the method of the invention is explant material which can be obtained from any plant organ or part thereof or other suitably differentiated plant tissue eg protoplasts. Such tissue can be selected from the group comprising stem, leaf, petal, hypocotyl section, apical meristem, ovaries, zygotic embryo per se, tuber, vascular bundle, pericycle, anther filament, and the like. Alternatively, a suitable explant material can be the somatic embryo per se. The plant tissue can be taken from any plant species of interest and includes plant tissue selected from monocotyledonous or dicotyledonous plants. A selection of plant types of interest can be found in the Handbook for Seedling Evaluation, J. Bekendam and R. Grob, ISTA, Zurich, Switzerland 1979 on pages 28–29 and further exemplified at index pages 122–126, herein incorporated by reference. Preferred plant types include those selected from the group comprising Cyclamen, Cucurbits, Lycopersicons, preferably table or edible Lycopersicons, Alliums, Begonias, Betas, Primulas, Brassicas, Capsicums, Cichoriums, Gerberas, Impatiens, Lactucas, Oryzas, Pelargoniums, Petunias, Violas, and Zeas. Most preferred are plant types selected from the group comprising Cyclamens, Cucurbits, Betas such as *Beta vulgaris* (sugar beets), Brassicas such as *B. oleracea* or *B. napus*, Violas, Pelargoniums, and Capsicums.

The liquid plant tissue culture medium suitable for use in the method of the invention can be any liquid plant tissue culture medium which is suitable for inducing and/or promoting embryogenesis. Examples of basic media commonly employed in the art include Gamborg's B5 medium (B5), Murashige and Skoog medium (MS), and variants thereof.

The present invention contemplates that a sufficient amount of auxin capable of inducing PEM formation be added to a suitable liquid culture medium containing explant or other suitable starting material in an initial induction phase, and that after such an initial induction phase, a further suitable liquid culture medium capable of promoting PEM growth and multiplication is employed in which auxin(s) concentration(s) are replenished at suitable intervals. It is accordingly advantageous to monitor the auxin concentration over time, using e.g. standard HPLC techniques known in the art to ensure that the development stage of the suspension is fixed at the PEM level. It is also important not to add too much auxin(s) to the plant tissue culture medium to avoid possible toxic side effects of the auxin(s) and yet maintain the PEMs in a viable state.

The liquid plant tissue culture medium for PEM growth and multiplication can be the initial induction phase plant tissue culture medium in which the auxin concentration and/or other essential components are simply replenished at suitable intervals such that the induction and promotion phases of somatic embryogenesis are able to take place; the initial induction phase medium can also be replaced by fresh plant tissue culture medium containing appropriate auxin concentrations at suitable intervals, whereby the liquid plant tissue culture medium may be the same or different from the appropriate but different liquid plant tissue culture medium initially employed. Thus, it can be appreciated that the actual plant tissue culture medium or media types employed are not critical to the invention provided that they are liquid and capable of being employed in inducing and/or promoting PEM formation in the presence of appropriate auxin concentration.

It can also be readily appreciated that the necessary auxin concentration will vary from plant species to plant species and may vary from plant variety to plant variety. The type and concentration of auxin giving the optimum results for a given variety, can be determined by standard tests. Depending on the plant variety it may be advantageous to employ a mixture of auxins. Examples of auxins and auxin-like compounds suitable for use in the method of the invention include indole acetic acid, indole butyric acid, naphthalene acetic acid and mixture thereof. The auxin level is maintained at such a concentration so as to promote the growth and formation of PEMs.

The auxin concentration is preferably maintained at a concentration of from about 0.1 mg/l to about 30 mg/l depending on PEM numbers or biomass and plant species of interest. A suitable mixture of auxins can include NAA and 2,4-D at appropriate concentrations. The effective auxin concentration of naphthalene acetic acid (NAA) will in general lie in the range of from about 0–20 mg/l and that of 2,4-D in the range of from about 0.1 mg/l up to about 10 mg/l, depending on plant species of interest. For example, cyclamen PEMs do not require the presence of NAA but do require the presence of 2,4-D at an initial concentration of from about 5–10 mg/l; lycopersicon PEMs have been found to require NAA at an initial concentration of 20 mg/l and 2,4-D at an initial concentration of 1 mg/l.

Depending on the plant variety and plant tissue culture medium employed, it may be advantageous to add a non-phytotoxic amount of cytokinin to the auxin containing medium to facilitate the auxin uptake.

The invention also provides a method of obtaining somatic embryos of substantially the same ploidy level in suspension culture which comprises:

i) Culturing explant material in contact with a liquid plant tissue culture medium comprising an effective amount of auxin or mixture of auxins sufficient to promote the induction of pro-embryogenic mass (PEM) formation;

ii) Multiplying the number of PEMs obtained in i) in contact with a suitable auxin containing liquid plant tissue culture medium;

iii) Collecting PEMs obtained in ii) and placing them in contact with a substantially auxin free liquid medium; and iv) Collecting embryos derived from the PEMs generated in iii).

Steps i) and ii) of this method have been discussed hereinabove. They can for example be carried out as follows:

Explant material is placed in a suitable liquid medium, such as B5 medium or MS medium, containing an auxin or a mixture of auxins at a concentration of from about 0.1 mg/l to about 30 mg/l depending on species of interest, and which is effective in inducing PEM formation. The explant material is cultured at a suitable density of from about 0.01 grams fresh weight/l to about 100 grams fresh weight/l culture, preferably from about 1.0 gram fresh weight/l to about 10 grams fresh weight/l for a period of time measured in weeks, during which time PEMs appear. The period of time can lie between from about 2 weeks up to about 14 weeks or more, typically from about 4 weeks to about 8 weeks, depending on the plant species of interest. Typically, PEMs obtained are separated out from the initial explant material culture, for instance, through medium dilution or medium replacement and further cultured on the same or a similar fresh liquid medium.

The PEMs obtained are capable of entering a growing or multiplying phase immediately under the same or similar ambient conditions to those required for induction of PEM formation. For convenience, this phase is referred to as a multiplication phase herein since increases in PEM numbers or PEM biomass are monitored and are seen to grow.

After induction of PEM formation is observed the liquid plant tissue culture medium is monitored such that auxin concentration is maintained at a level sufficient to promote PEM growth and multiplication without significant PEM development. The multiplication phase may involve subculturing in regular dilutions of liquid plant tissue culture medium of choice such that auxin levels are controlled at a level sufficient to promote PEM multiplication for a suitable time interval. Alternatively, PEMs may be separated from the initial explant material culture and placed in an auxin containing plant tissue culture medium and simply permitted to multiply to a desired PEM biomass by using a fed-batch or a continuous culture system. Typically, this involves maintaining the auxin concentration above a level of about 0.1 mg/l for a period of time. The period of time for the multiplication phase can be measured in years depending on how many PEMs are required for converting into true somatic embryos, however, usually the multiplication phase is measured in months or weeks, such as between about 2 to about 30 weeks depending on the amount of PEM biomass required. Once in the multiplication phase PEMs can be collected at any time for placement into substantially auxin-free plant tissue culture medium where they can then proceed to develop into true somatic embryos. This can involve sieving out as described herein ie selecting PEM fractions of a certain size which can pass through suitably sized sieves, (eg a 150 µm pore sized sieve) but are retained on a smaller sized sieve (eg a 100 mm pore sized sieve).

The PEM formation and multiplication is advantageously influenced by supplementation of a suitable carbon energy source, conveniently a soluble carbohydrate such as sucrose, glucose or raffinase, to the liquid plant tissue culture medium.

Typical carbohydrate concentrations lie in the range of from 15 g/l to 90 g/l, preferably of from 20 g/l to 60 g/l of plant tissue culture medium.

The multiplication phase can be performed in flasks or in a bioreactor. Bioreactors are known in the art for culturing of cell suspensions for the manufacture of secondary cell metabolites, however, the use of bioreactors for PEM culturing has not been described hitherto. We have found that bioreactors can be useful in the production of very large numbers of PEMs in relatively short time intervals.

For convenience, packed cell volumes from PEM suspension cultures are inoculated into a suitable medium containing a sufficient amount of a suitable carbon energy source, such as, for example sucrose, glucose and raffinose at between about 15 g/l up to about 90 g/l or more, preferably between about 20 g/l to about 60 g/l, depending on the PEM species of interest, in a suitable bioreactor. Preil W. and Beck A. [(1991) Acta Horticulturae 289, Plant Technology: 179–192] describe somatic embryogenesis in bioreactors using vibromixers, however, there is no indication in that study that PEM formation and multiplication is carried out prior to the development of PEMs into somatic embryos. The use of vibromixers in bioreactors on PEM suspension cultures has been found to significantly increase the life span of PEMs over time, help increase the PEM biomass, reduce PEM biomass loss and prevent clumping of PEMs. A vibromixer fitted with a perforated mixing plate or stirring disc (available from Applikon BV, The Netherlands and Chemap AG, Switzerland, respectively) positioned in a fixed plane in a bioreactor and permitted to vibrate substantially in that fixed plane has resulted in PEM suspension cultures being mixed or stirred without significant loss in PEM biomass.

Preferably, the vibromixer is vibrated in substantially the vertical plane. A typical operation frequency of a vibromixer for use in the method of the invention is 50 Hz; the amplitude is conveniently in the order of ±6 mm or less. Once a PEM biomass is attained which is capable of giving rise to a desired number of somatic embryos, the PEMs can be placed in contact with a substantially auxin free liquid plant tissue culture medium in which they are able to develop into somatic embryos.

The PEM suspension is advantageously aerated. This can be effected in a manner known per se. Where a vibromixer is employed, the air can for example be sparged into the vibromixer reactor employing a porous sparging device.

It follows from the above and the examples that the optimum conditions for the various parameters such as type and concentration of the auxins, the presence of a cytokinin, the energy (carbohydrate) source, the stirring or vibration frequency, the oxygen supply, the light intensity and wavelength will vary depending on the plant material employed. Such optimum conditions can be determined employing standard tests (as illustrated in the examples).

The subsequent steps iii) and iv) of the method of obtaining somatic embryos according to the invention, may be carried out as follows:

The promotion of PEM development to somatic embryos can be achieved by placing the PEMs in an auxin free plant tissue culture medium. The viable PEMs are capable of developing into somatic embryos. Prior to the transfer in an auxin free medium, the PEMs are advantageously sieved, e.g. through nylon mesh, to select the PEM size fraction generating most efficiently the desired somatic embryos. A too high content of non-viable PEMs will inhibit somatic embryo formation. In general it is desirable to employ PEMs comprising at least 5%, preferably at least 10%, more preferably at least 15% of viable PEMs. The optimum size fraction can be determined by standard screening tests.

The PEMs of a selected size can be collected by for example sieving or any other size sorting means in the art. The skilled person in the art will appreciate that the size of desirably sized PEMs (i.a. the PEM fraction having a high content of viable PEMs) will vary from species to species as detailed herein.

A sieved fraction of PEMs is one which is obtained by passing PEMs through a filtering means such as net meshes of known pore size, eg a nylon mesh in order to obtain PEMs within a given size range. PEMs can be of any size up to about 1 mm in diameter depending on plant species, however, aggregates of PEMs can be up to 5 mm in diameter. Generally speaking, the desirable size of individual PEMs is in the order of µm. It has been found that the size of the PEMs is critical to the obtention of single somatic embryos derived therefrom. Preferably, a collected PEM fraction is one wherein each PEM therein is capable of giving rise to one somatic embryo under appropriate conditions. Naturally, the size of the particular viable, sieved PEM fraction varies from plant species to plant species. For example the most useful PEM fraction for cucumber is the one where the size of the PEMs is between about 100 µm– to about 150 µm; the PEM fraction for cyclamen from about 150 µm to about 300 µm. In a preferment, the PEM fraction is one in which each PEM is capable of giving rise to at least one somatic embryo, preferably to a single somatic embryo.

The substantially auxin free liquid plant tissue culture medium is one which is capable of permitting PEMs to develop into somatic embryos. Thus it is contemplated that the substantially auxin free liquid plant tissue culture medium can be an auxin depleted plant tissue culture medium wherein residual levels of auxin may be present but which auxin levels, if any, do not substantially interfere with the development of PEMs into somatic embryos, or it can be an auxin free plant tissue culture medium. Naturally, the skilled person in the art will appreciate that the substantially auxin free plant tissue culture medium can be placed either in a flask or in a suitable bioreactor, for example one fitted with a vibromixer depending on how many somatic embryos are desired. Somatic embryos obtained can then be converted into plants using methods known in the art. Thus, by monitoring the PEM biomass it is possible to attain large numbers of somatic embryos in commercial quantities.

The auxin free medium comprises conveniently a soluble carbohydrate energy source at a concentration of from 15 g/l to 90 g/l, preferably from 20 g/l to 60 g/l. Suitable carbohydrate energy sources include sucrose, glucose and raffinose.

Commercial somatic embryo quantities can range in value from a few hundreds (eg 500), to several millions (eg 3,000,000) or more depending on requirements of the customer. For instance, if a requirement is for about 200,000 plants, PEM multiplication is continued until a PEM biomass is reached which is substantially capable of giving rise to about 200,000 somatic embryos. Such PEMs are then placed in contact with auxin-free liquid plant tissue culture medium where they can develop into somatic embryos.

Once true somatic embryos develop in the substantially auxin free plant tissue culture medium, they can be separated out of the auxin free plant tissue culture medium and converted into plants using techniques commonly employed in the art.

The somatic embryos are conveniently separated from the non-viable PEMs prior to commercial use. This can be done in a manner known per se. The non-viable PEMs are in general smaller than the somatic embryos. The somatic embryos can for example be isolated manually, by sieving or cell sorting.

In a further embodiment of the invention there are provided batches of somatic embryos comprising somatic embryos which have substantially all the same ploidy level. Batches of somatic embryos may comprise between several hundreds to tens of thousands or more depending on commercial requirements. Preferably, batches of somatic embryos comprise substantially diploid somatic embryos or substantially tetraploid somatic embryos. A batch of somatic embryos can simply be a suspension of somatic embryos from which liquid media has been drained wherein the somatic embryos are placed in a suitable container. The ambient environment of the container may have a high relative humidity eg 100%, and may be maintained at a suitably cool temperature above 0° C., up to about 15° C. Somatic embryos stored in this way can be maintained for up to about 4 days. Alternatively, the somatic embryos may be subjected to a desiccation process, frozen, pelleted, encapsulated in a gel and the like.

The invention provides further somatic embryo suspension cultures different from Daucus, comprising somatic embryos having substantially all the same ploidy level. Preferred somatic embryos are diploid or tetraploid. The somatic embryos are derived from dicotyledonous or monocotyledonous explant material.

There now follow examples illustrating the invention. It is to be understood that the examples are not to be viewed as limiting the scope of the invention in any way.

EXAMPLE 1

Initiation of Embryogenic Cyclamen Cell Cultures and Somatic Embryos therefrom

Seeds of Cyclamen variety "Concerto Scarlet" (Sluis and Groot) are surface sterilized with 70% ethanol (for 2 minutes) and with a 1.5% solution of sodium hypochlorite (for 45 minutes), then washed thoroughly with sterile water (3×).

The seeds are germinated on moist paper for between 2–4 weeks at 23° C., and the emerged tuber is used as explant material. Three tubers are cultured in 10 ml of basic B5 medium (commercially available from Duchefa Biochemie BV, Haarlem, The Netherlands), supplemented with 20 g/l sucrose, 10 mg/l 2,4-D, 100 mg/l myo-inositol, 1.0 mg/l nicotinic acid, 1.0 mg/l pyridoxine HCl and 10 mg/l thiamine HCl on a rotary shaker (G10 gyrorotary shaker, New Brunswick Scientific, Edison, N.J. U.S.A.) at 100 rpm in the dark, at 23° C. After 7 days the medium is replaced with fresh medium. After a further 7 days, the culture is diluted (5×) to a volume of 50 ml with fresh medium. After a further 7 days the central piths comprising vascular bundles and pericycle of the tuber explant material from the diluted culture are separated from the tuber explant material and sub-cultured apart from the rest of the tubers in 25 ml of basic B5 medium supplemented with 20 g/l sucrose, 100 mg/l myo-inositol, 1.0 mg/l nicotinic acid, 1.0 mg/l pyridoxine HCl, 10 mg/l thiamine HCl, 5 mg/l 2,4-D, and 1 mg/l kinetin. The subcultures are diluted weekly two fold, for 4 weeks. Pro-embryogenic masses appear at about 4 weeks. PEMs are multiplied by further sub-culturing as described above for a period of 2 weeks. PEMs are able to develop into viable, true somatic embryos by further culturing on auxin and cytokinin free B5 medium, supplemented with 20 g/l sucrose, 100 mg/l myo-inositol, 1.0 mg/l nicotinic acid, 1.0 mg/l pyridoxine HCl, and 10 mg/l thiamine HCl.

EXAMPLE 2

Initiation of Embryogenic Cyclamen Cell Suspension Cultures and Somatic Embryos therefrom.

Cyclamen seeds (cv Concerto Scharlaken Othello, of Zaadunie BV) are surface sterilized with 70% ethanol (for 2 minutes) and 1% sodium hypochlorite solution (for 45 minutes) and washed thoroughly with sterile water (3×). The seeds are germinated on moist paper for between two to five weeks in the dark at 23° C. Emerged tubers are used as explant material and cut into between two to eight pieces. Ploidy level of the explant material is measured according to the teaching of De Laat, A. M. M. et al. (1987) Plant Breeding 99:303–307, and found to be diploid.

Explant material from three tubers is cultured in 10 ml of basic B5 medium (Duchefa Biochemie BV, Haarlem, The Netherlands) supplemented with sucrose at 20 g/l, 2,4-dichlorophenoxyacetic acid at 5 mg/l, and kinetin at 1 mg/l in a 50 ml flask on a rotary shaker (100 rpm) in the dark and at a temperature of 23° C. All flasks are covered with aluminium foil. After one week the culture is diluted five fold with basic B5 medium supplemented with 20 g/l sucrose, 5 mg/l 2,4-D, 100 mg/l myo-inositol, 1.0 mg/l nicotinic acid, 1.0 mg/l pyridoxine HCl 10 mg/l thiamine HCl and 1 mg/l kinetin to a volume of 50 ml in a 250 ml flask. After a further two weeks the culture contains PEMs which are separated from the rest of the culture with a pipette having a wide nozzle, and cultured separately. PEMs are identified visually as cell clumps consisting essentially of small, round, cytoplasmic cells. At this stage PEMs are either identified as single clumps of cells or a number of clumps of cells attached to each other. The cultures are subcultured every two weeks by inoculating 1 ml of packed cells in basic B5 medium supplemented with with 20 g/l sucrose, 5 mg/l 2,4-D, 100 mg/l myo-inositol, 1.0 mg/l nicotinic acid, 1.0 mg/l pyridoxine HCl, 10 mg/l thiamine HCl and 1 mg/l kinetin to a final volume of 50 ml, in a 250 ml flask using a pipette having a wide nozzle. Packed cell volume (PCV), ie total cell mass after centrifugation for $PCV_{initial}$ and $PCV_{final}$ is determined by centrifuging samples from cultures for 2 mins. at 700× g. The embryogenic cell line generally grows with a doubling time of between about 4 to 6 days as calculated from measurements of $PCV_{initial}$ and $PCV_{final}$ using the formula of Schlegel, H. G. (1981) Allgemeine Microbiologie, Thieme, Stuttgart, page 190. The embryogenic cell line obtained in this way is maintained for at least 45 weeks and is genetically stable, ie the ploidy level is diploid, the same as that of the original explant material.

PEMs are selected by sieving the PEM culture through nylon meshes having a pore size of 250 μm and 100 μm respectively. Eight days after subculturing the highest number of PEMs/ml is achieved. This fraction gives rise to optimal embryo development and the highest number of embryos per PCV of the PEM culture. The number of PEMs sieved generally ranges from 1000 to 5000 PEMs/ml PCV.

After sieving, PEMs are washed and inoculated into development medium, ie MS or B5 medium supplemented with sucrose or glucose to a concentration of 174 mM. 25 to 50 PEMs/ml are cultured in a flask sealed with aluminium foil and nescofilm (Bando chemicals Ind. LTD, Japan). After three to four weeks torpedo shaped embryos are formed which resemble zygotic embryos. Using this method 250,000 embryos are produced. Employing flow cytometrical analysis techniques as described by De Laat A. M. M. supra on a random sample of the embryo culture, DNA content of 500 somatic embryos is assessed. All embryos are found to be diploid.

Conversion (ie germination) of cyclamen embryos comprises tuber formation followed by adventitious root formation and is induced by culturing the embryos on a liquid medium ie MS or B5 medium having a glucose or sucrose content of about 116 mM or 58 mM respectively. Tuber formation is defined as the development from the hypocotyl of a tuber or tuber-like structure. Further development of the cotyledon forming the first leaf can occur either in liquid medium or on solid medium such as perlite, sterilized soil and the like.

Converted embryos are sown directly on perlite or potting soil, under sterile conditions (in the presence of a carbon source) or under non-sterile conditions (no carbon source added) and show cotyledon formation after two to four weeks in the dark at 18° to 20° C. A high relative humidity of about 90% is employed. Over 90% of embryos convert to the cotyledon stage under sterile conditions. Once the cotyledon appears resultant plantlets are placed in the light and hardened before transfer to the greenhouse.

EXAMPLE 3

Initiation of Embryogenic Tomato Cell Cultures

Seeds of tomato variety, "Manhattan" (Sluis and Groot) are surface sterilized with 70% ethanol (for 2 minutes) and a 1.5% solution of sodium hypochlorite for 15 minutes then washed thoroughly with sterile water (3×). The seeds are germinated on moistened paper over 3 days at a temperature of 23° C. Complete seedlings are collected, and each seedling is cut into 4 pieces which are then used as explant material. 10 seedlings are cut up in this manner and are incubated in 15 ml of liquid basic B5 medium (commercially available from Duchefa Biochemie BV, Haarlem, The Netherlands) supplemented with sucrose at 20 g/l, 20 mg/l NAA, 1 mg/l 2,4-D, 1 mg/l kinetin, 100 mg/l myo-inositol, 1 mg/l nicotinic acid, 1 mg/l pyridoxine HCl, and 10 mg/l thiamine HCl on a rotary shaker at 100 rpm at 23° C. under a cyclable 16 hr light period and 8 hr darkness period. The culture medium is monitored for auxin concentration using HPLC techniques known in the art. Once the auxin concentration falls to below 0.1 mg/l, after about 7 days, 15 ml of fresh basic B5 medium (commercially available from Duchefa Biochemie BV, Haarlem, The Netherlands) supplemented with sucrose at 20 g/l, 20 mg/l NAA, 1 mg/l 2,4-D, 1 mg/l kinetin, 100 mg/l myo-inositol, 1 mg/l nicotinic acid, 1 mg/l pyridoxine HCl, and 10 mg/l thiamine HCl is added to make up the volume to 30 ml of culture. This culture is sub-cultured every 4–7 days by permitting the explant material and cells to settle for 15 minutes and refreshing the culture by taking off 15 mls of used medium and replenishing with 15 mls of fresh medium. After about 4–7 weeks after initial culturing of explant material pro-embryogenic masses (PEMs) are observed. PEMs are multiplied by further sub-culturing as described above for a period of 2 weeks. The PEMs are further subcultured on auxin free basic B5 medium supplemented as above excluding NAA, 2,4-D and kinetin and true somatic embryos are observed.

EXAMPLE 4

Initiation of Embryogenic Tomato Cell Cultures

Seeds of tomato variety, "Majorca" (Sluis and Groot) are surface sterilized with 70% ethanol (for 2 minutes) and a 1.5% solution of sodium hypochlorite for 15 minutes then washed thoroughly with sterile water (3×). The seeds are germinated on moistened paper for 7 days at a temperature of 23° C. in the dark. Cotyledons are collected and cut into pieces which are used as explant material. 6 cotyledons of 3 seedlings are cut up in this manner and are incubated in 15 ml of liquid medium A (see Table 1) supplemented with 4 mg/l 2,4-D and 0.5 mg/l kinetin on a rotary shaker at 100 rpm at 23° C. in the dark. After 14 days, 35 ml of fresh medium A (see Table 1) including hormones as described above, is added. The culture is sub-cultured every 14 days by diluting 2× in fresh medium A (see Table 1), supplemented with hormones as above. About 4 weeks after initial culturing of explant material PEMs are observed. PEMs are multiplied by further sub-culturing as described above.

TABLE 1

| Composition of medium A | |
|---|---|
| Macro elements | g/l |
| $NH_4NO_3$ | 1.20 |
| $(NH_4)_2SO_4$ | 0.66 |
| $KH_2PO_4$ | 0.55 |
| $KNO_3$ | 1.01 |
| $MgCl_2.6H_2O$ | 0.30 |
| $CaCl_2$ | 0.22 |
| Citric Acid | 0.5 |
| Sucrose | 20 |

Micro elements 2 ml stock solution/l
Vitamins Gamborg B5 (1 mg/l) 1 ml stock solution/l
pH adjusted to 5.8 using KOH (1M),
Micro elements (Stock solution)

| | g/l |
|---|---|
| $FeSO_4.7H_2O$ | 6.9 |
| $CuSO_4.5H_2O$ | 0.65 |
| $CoCl_2.6H_2O$ | 0.12 |
| $MnCl_2.4H_2O$ | 2.97 |
| $NaMoO_4.2H_2O$ | 0.24 |
| KI | 0.041 |
| $HBO_3$ | 1.5 |
| $ZnSO_4.7H_2O$ | 4.3 |
| $NiSO_4.6H_2O$ | 0.39 |
| citric acid | 2 |
| pH = 2.3 | |
| Vitamins Gamborg B5 (Duchefa); stock solution supplemented with: | |
| myo-Inositol | 100 g/l |
| Nicotinic acid | 1 g/l |
| Thiamin-HCl | 1 g/l |

EXAMPLE 5

Initiation of Embryogenic Cucumber Cell Suspension Cultures and Somatic Embryos therefrom.

Seeds of cucumber variety "Pandorex" (Sluis and Groot) are surface sterilized with 70% solution of ethanol (for 2 minutes) and a 1.5% solution of sodium hypochlorite (for 45 minutes), then washed thoroughly with sterile water (3×). The cucumber seeds are germinated on moistened paper for 2 days at 23° C. The emerged radicle from the seed is used as explant material. 15 radicles are cultured in 10 ml of basic liquid MS medium plus vitamins (commercially available from Duchefa Biochemie BV, Haarlem, The Netherlands) supplemented with sucrose at 20 g/l, 2 mg/l 2,4-D and 1 mg/l kinetin on a rotary shaker at 100 rpm in the dark at a temperature of 23° C. The culture medium is monitored for auxin concentration using HPLC techniques known in the art. After the auxin concentration falls to <0.1 mg/l, after about 5 days, the culture is diluted 5× to 50 ml basic liquid MS medium plus vitamins (commercially available from Duchefa Biochemie BV, Haarlem, The Netherlands) supplemented with sucrose at 20 g/l, 2 mg/l 2,4-D and 1 mg/l kinetin. Cultures are sub-cultured every two weeks by diluting the culture 2× with basic liquid MS medium plus vitamins (commercially available from Duchefa Biochemie BV, Haarlem, The Netherlands) supplemented with sucrose at 20 g/l, 2 mg/l 2,4-D and 1 mg/l kinetin. 8 weeks later pro-embryogenic masses appear.

The PEM cultures are then further subcultured by inoculating 0.4 ml of packed cell volume in 50 ml every two weeks in medium A (of Table 1) supplemented with 10 mg/l 2,4-D and 0.5 mg/l kinetin. The doubling time of the cucumber cell line is about 2.7 days as determined using the formula of Schlegel (supra). PEMs are selected by sieving the culture through nylon meshes of pore sizes 150 μm and 100 μm respectively, for PEMs between 100–150 μm in size. The 100–150 μm fraction produces the highest number of single somatic embryos per PCV of the PEM culture. The PEMs from this cell line are either diploid or tetraploid. The ratio between diploid and tetraploid cells remains constant over time for over two years on liquid medium A supplemented with 10 mg/l 2,4-D and 0.5 mg/l kinetin, as measured by the method of De Laat A. M. M. et al supra. PEMs produce diploid as well as tetraploid plants. The measured ratio of diploidy:tetraploidy is reflected in the PEMs as well as the plants.

PEMs are developed into true somatic embryos by culturing the PEMs on auxin and cytokinin free MS medium supplemented with sucrose at 20 g and 5 μM ABA.

EXAMPLE 6

Manipulation of Embryogenic Cucumber cell lines to obtain 100% diploid or 100% tetraploid suspension cultures.

The suspension of example 5 consists of diploid and tetraploid PEMs which gives rise to the development of embryos with the same ploidy levels.

Individual PEMs of about 2 mm diameter are picked out from a 13 week old cell suspension initiated according to the method of example 5. Measurement of the individual PEMs for the ploidy level following the method of De Laat et al. (1987) Plant Breeding 99, 303–307 shows that the PEMs are either 100% diploid or 100% tetraploid. Further culturing of individual PEMs over a period of fifteen weeks (ie subcultures performed every two weeks) in basic MS liquid medium as described in Example 5 gives rise to cell lines consisting of 100% diploid or 100% tetraploid cells as determined using the method of De Laat et al. supra. Diploid PEMs give rise to diploid embryos and diploid plants. Tetraploid PEMs give rise to tetraploid embryos and tetraploid plants.

EXAMPLE 7

Manipulation of Embryogenic Cucumber cell lines to obtain 100% diploid or 100% tetraploid suspension cultures.

Plants of cucumber variety "Pandorex" (Sluis and Groot) are grown under sterile conditions using the method of example 3. Ovaries of about 1 cm in size are used as one explant. Measurement of the ploidy level following the method of De Laat et al supra shows that the explant is completely diploid. About half of the fruit is chopped into slices of about 0.5 mm thickness and cultured in 10 ml of basic liquid MS medium plus vitamins (commercially available from Duchefa Biochemie BV, Haarlem, The Netherlands) supplemented with sucrose 20 g/l, 2 mg/l 2,4-D and 1 mg/l kinetin on a rotary shaker at 100 rpm in the dark at a temperature of 23° C. The culture medium is monitored for auxin concentration employing HPLC techniques known in the art. After the auxin concentration falls to <0.1 mg/l, after about 5 days, the culture is diluted 5× to 50 ml with basic liquid MS medium plus vitamins (commercially available from Duchefa Biochemie BV, Haarlem, The Netherlands) supplemented with sucrose 20 g/l, 2 mg/l 2,4-D and 1 mg/l kinetin. Cultures are sub-cultured every two weeks by diluting the culture 2× with MS medium supplemented as above.

8 weeks later pro-embryogenic masses appear. The PEM cultures are subcultured as described in example 5 in medium A (of Table 1) supplemented with 10 mg/l 2,4-D and 0.5 mg/l kinetin. 0.4 ml of packed cell volume is inoculated in 50 ml of medium A supplemented with 10 mg/l 2,4-D and 0.5 mg/l kinetin. The doubling time of the cucumber cell line is about 2.7 days in medium A (Table 1) as determined using the formula of Schlegel (supra). The ploidy level of the PEM suspension is determined following the method of De Laat et al supra and is found to be diploid. PEMs are selected by sieving the culture through nylon mesh for PEMs between 100–150 μm in size. PEMs are developed into true somatic embryos by culturing selected PEMS on auxin and cytokinin free MS medium supplemented with 20 g/l sucrose. Using this method 200,000 embryos are produced in four weeks from PEM culture. The ploidy level of 500 somatic embryos selected at random are all found to be diploid using the method of De Laat et al supra.

EXAMPLE 8

Maintenance of stable PEM suspensions with respect to ploidy level.

Cucumber PEM suspensions are grown in medium A (Table 1), supplemented with 10 mg/l 2,4-D and 0.5 mg/l kinetin. During subculturing macro elements and micro elements are held in excess at each subculturing step to PEM requirements such that shortages of these elements does not occur during the subculturing interval (ie 2 weeks). Auxin levels (ie 10 mg/l 2,4-D) are maintained in the same way. Kinetin (ie 0.5 mg/l) is added to the medium at the beginning of subculturing and allowed to deplete from the medium in four days. Monitoring the auxin concentration over time using standard HPLC techniques known in the art ensures that the developmental stage of the suspension is fixed at the PEM level. Embryogenic diploid PEM suspensions are maintained for up to 2 years in medium A (Table 1) supplemented with 10 mg/l 2,4-D and 0.5 mg/l kinetin and show a stable ploidy level. Embryogenic tetraploid PEM suspensions are maintained for 6 months showing a stable ploidy level. This ploidy level is maintained until embryo development is initiated.

EXAMPLE 9

Initiation of Embryogenic Sugarbeet PEM Suspension Cultures and somatic embryos therefrom.

Seeds of sugarbeet (Hilleshog AB, Sweden) are surface sterilized with 70% solution of ethanol (for 2 minutes) and a 1.5% solution of sodium hypochlorite (for 45 minutes), then washed thoroughly with sterile water (3×). The sugarbeet seeds are germinated on moistened paper for 7 to 14 days at 23° C. The cotyledons from germinated seeds are used as explant material. 6 cotyledons are cultured in 10 ml of liquid medium A (Table 1 supplemented with 10 mg/l 2,4-D and 0.5 mg/l kinetin on a rotary shaker at 100 rpm in the dark at a temperature of 23° C. The culture is diluted 5× with liquid medium A (Table 1) supplemented with 10 mg/l 2,4-D and 0.5 mg/l kinetin to 50 ml after one or two weeks. Cultures are sub-cultured every two weeks by diluting the culture 2× with medium A (Table 1) supplemented as above or by replacing the medium with fresh medium A supplemented as described above. After 4 to 6 weeks somatic embryos appear on the explant tissue. The embryos are picked off the explant and cultured separately. 4 weeks later cultured embryos produce PEMs. The PEM cultures are further subcultured by replenishing with medium A of Table 1 supplemented with 10 mg/l 2,4-D and 0.5 mg/l kinetin.

PEMs are collected by sieving the PEM suspension first on nylon mesh having a pore size of 500 μm and then on nylon mesh having a pore size of 100 μm. The PEM fraction 100–500 μm generally gives rise to predominantly single somatic embryos. The PEMs are cultured on auxin and cytokinin free medium A supplemented with 10 mg/l 2,4-D and 0.5 mg/l kinetin into true somatic embryos.

EXAMPLE 10

Initiation of Embryogenic Pepper PEM Suspension Cultures.

Seeds of pepper, (cv Gedeon of Sluis en Groot) are surface sterilized with 70% solution of ethanol (for 2 minutes) and a 1.5% solution of sodium hypochlorite (for 45 minutes), then washed thoroughly with sterile water (3×). The pepper seeds are germinated on moistened paper for 7 to 14 days at 23° C. The cotyledons from the germinated seed are used as explant material. 6 cotyledons are cultured in 10 ml of liquid medium A (Table 1) supplemented with 10 mg/l 2,4-D on a rotary shaker at 100 rpm in the dark at a temperature of 23° C. The culture is diluted 5× to 50 ml after two weeks. Cultures are sub-cultured every two weeks by diluting the culture 2× as described above or replacing the medium by fresh liquid medium A (Table 1) supplemented with 10 mg/l 2,4-D. After 2 to 4 weeks embryos appear at the cut edges of the explant. The embryos are taken off the explant and removed from the culture and subcultured on liquid medium A (Table 1) supplemented with 4 mg/l 2,4-D and 0.5 mg/l Zeatin. 4 weeks later pro-embryogenic masses appear. PEMs are multiplied by further sub-culturing as described above. PEMs are collected by sieving the suspension as described in example 5. The fraction 100–500 μm gives rise to predominantly single somatic embryos. The PEMS are cultured on auxin and cytokinin free medium A (Table 1).

EXAMPLE 11

Initiation of Embryogenic Viola PEM Suspension Cultures and somatic embryos therefrom.

Seeds of Viola, (cv Delta violet of Sluis en Groot) are surface sterilized with 70% solution of ethanol (for 2 minutes) and a 1.5% solution of sodium hypochlorite (for 30 minutes), then washed thoroughly with sterile water (3×). Viola seeds are germinated on moistened paper for 7 to 14 days at 23° C. The cotyledons from the germinated seed are used as explant material. 6 cotyledons are cultured in 10 ml of liquid medium A (Table 1) supplemented with 4 mg/l 2,4-D and 0.1 mg/l kinetin on a rotary shaker at 100 rpm in the dark at a temperature of 23° C. The culture is diluted 5× with liquid medium A (Table 1) supplemented with 4 mg/l 2,4-D and 0.1 mg/l kinetin to 50 ml after two weeks. Cultures are sub-cultured every two weeks by diluting the culture 2× or replacing the medium by fresh liquid medium A (Table 1) supplemented with 4 mg/l 2,4-D and 0.1 mg/l kinetin. After 8 to 10 weeks pro-embryogenic masses appear. PEMs are multiplied by further sub-culturing as described above. PEMs are collected by sieving the suspension as described in example 5 except that the nylon mesh pore sizes used are 50 μm and 250 μm. The PEMs are cultured on auxin and cytokinin free medium A (Table 1) supplemented as above and developed into single somatic embryos.

EXAMPLE 12

Initiation of Embryogenic Pelargonium PEM Suspension Cultures

Seeds of Pelargonium, (cv Pulsar red of Sluis en Groot) are surface sterilized with 70% solution of ethanol (for 2 minutes) and a 1.5% solution of sodium hypochlorite (for 30 minutes), then washed thoroughly with sterile water (3×). Pelargonium seeds are germinated on moistened paper for 7 to 14 days at 23° C. The cotyledons from the germinated seed are used as explant material. 6 cotyledons are cultured in 10 ml of liquid medium A (Table 1) supplemented with 4 mg/l 2,4-D and 0.1 mg/l kinetin on a rotary shaker at 100 rpm in the dark at a temperature of 23° C. The culture is diluted 5× with liquid medium A (Table 1) supplemented with 4 mg/l 2,4-D and 0.1 mg/l kinetin to 50 ml after one week. Cultures are sub-cultured every two weeks by diluting the culture 2× with liquid medium A (Table 1) supplemented with 4 mg/l 2,4-D and 0.1 mg/l kinetin or replacing the medium with fresh medium A supplemented as described above.

After 4 to 6 weeks pro-embryogenic masses appear. PEMs are multiplied by further sub-culturing as described above. PEMs are collected by sieving the suspension as described in example 5 except that the nylon mesh pore size used is 250 μm and 50 μm. The PEM fraction of 50–250 μm gives rise to predominantly single somatic embryos. PEMs are cultured on auxin and cytokinin free medium A (Table 1) and develop into single somatic embryos.

EXAMPLE 13

Multiplying PEM Biomass in Bioreactors

4×8 ml PCV is collected from cucumber PEM suspension cultures subcultured as described in example 5 and inoculated into 4 bioreactors (Applikon Dependable Instruments B.V.) comprising two conventional 2 l bioreactors fitted with impellers, and two bioreactors fitted with vibromixers commercially available from Chemap AG, each containing 1 l medium A (Table 1) supplemented with 10 mg/l 2,4-D and 0.5 mg/l kinetin. Air is sparged into the vibromixer reactors via a 15 μm porous sparging device located at the end of the vibrator shaft positioned towards the bottom of the reactor chamber. The dissolved oxygen concentration in one of the vibromixer reactors is determined at 40%, and in the other at 97% following standard techniques known in the art. Vertically positioned Vibromixers are operated at a frequency of 50 Hz and a maximum amplitude of ±6 mm. The vibromixers are positioned such that the vibrating motion is in the vertical plane and horizontal motion is kept to a minimum. Stirring discs are fitted on the end of the vibrating shaft such that fluid is directed in a current loop drawing the cell suspension from the periphery of the reactor vessel towards the base and then upwards.

Air is sparged into the conventional bioreactors at the bottom of the bioreactor via a sparging tube fitted with a 15 μm porous sparger. Dissolved oxygen concentration is determined as per the above at concentrations of 40% and 97% respectively. Stirring speed of the impeller is maintained at about 150 rpm ±50 rpm.

6 days after inoculation doubling time is determined, PEMs are sieved from the PEM suspension and PEMs/ml PCV are determined as described in example 5.

The use of vibromixers gives rise to greater numbers of PEMs per unit volume (Table 2; FIG. 1).

TABLE 2

| Apparatus | Doubling Time (Days) | PEMs/ml PCV |
| --- | --- | --- |
| Impeller (40% $DO_2$)[1] | 2.3 | 200 |
| Impeller (97% $DO_2$) | 2.7 | 620 |
| Vibromixer (40% $DO_2$) | 2.8 | 2284 |
| Vibromixer (97% $DO_2$) | 3.3 | 3710 |

[1]$DO_2$ = Dissolved oxygen

EXAMPLE 14

Multiplying PEM Biomass in Vibromixer Bioreactors

2×8 ml PCV is collected from cucumber PEM suspension cultures subcultured as described in example 3 and inoculated into two vibromixer bioreactors (Applikon Dependable Instruments B. V.) comprising two 2 l bioreactors fitted with vibromixers commercially available from Chemap AG. One bioreactor contains 1 l medium A (Table 1), supplemented with 10 mg/l 2,4-D and 0.5 mg/l kinetin, the other also contains 1 l of medium A supplemented as above with the exception that the sucrose concentration is at 55 g/l. Air is sparged into the vibromixer reactors via a 15 μm porous sparging device located at the end of the vibrator shaft near the base of the reactor chamber. The dissolved oxygen concentration is determined at 97% following standard techniques known in the art. Vibromixers are operated at a frequency of 50 Hz and a maximum amplitude of ±6 mm.

The vibromixers are positioned such that the vibrating motion is in the vertical plane while lateral or horizontal motion is kept to a minimum. Stirring discs are fitted on the end of the vibrating shaft such that fluid flows in a current loop drawing the cell suspension from the periphery of the reactor vessel towards the base and then upwards.

6 days after inoculation doubling time is determined, PEMs are sieved from the PEM suspension and PEMs/ml PCV are determined as in example 5. Results are shown below in Table 3.

TABLE 3

| Apparatus | Doubling Time (Days) | PEMs/ml PCV |
|---|---|---|
| Vibromixer (97%, 20 g/l sucrose) | 3.3 | 2284 |
| Vibromixer (97%; 55 g/l sucrose) | 2.9 | 6000 |

EXAMPLE 15

Comparison of Viability of PEMs over time from Stirred Bioreactors versus Vibromixer Bioreactors.

3×8 ml PCV is collected from cucumber PEM suspension cultures subcultured as described in example 5 and inoculated into 3 bioreactors (Applikon Dependable Instruments B. V.) comprising one conventional 2 l bioreactor fitted with an impeller containing 1 l medium A (Table 1), supplemented with 10 mg/l 2,4-D and 0.5 mg/l kinetin, and two bioreactors fitted with vibromixers commercially available from Chemap AG, one containing 1 l medium A supplemented as above and the other also containing 1 l medium A supplemented as above with the exception that the sucrose concentration is at 55 g/l.

Air is sparged into the vibromixer reactor via a 15 μm porous sparging device located at the end of the vibrator shaft towards the bottom of the reactor Chamber. The dissolved oxygen concentration in the vibromixer reactor is determined at 97% following standard techniques known in the art. Vibromixer is operated at a frequency of 50 Hz and a maximum amplitude of ±6 mm. The vibromixer is positioned such that the vibrating motion is in the vertical plane and horizontal vibrating motion is kept to a minimum. Stirring disc is fitted on the end of the vibrating shaft such that fluid flows in a current loop drawing the cell suspension from the periphery of the reactor vessel towards the base and then upwards.

Air is sparged into the conventional bioreactor at the bottom of the bioreactor via a sparging tube fitted with a 15 μm porous sparger. Dissolved oxygen concentration is determined as per the above at a concentration of 97%. Stirring speed of the impeller is maintained at about 150 rpm ±50 rpm.

PEMs/ml PCV is determined at the start of culturing and doubling time is determined at 6 and 14 days as described in example 5.

Results show that the number of PEMs in a stirred bioreactor decreases significantly over time, whereas the number of PEMs in a vibromixer remains almost constant over time at a sucrose concentration of 20 g/l. PEM numbers are shown to increase up to 3× within 6 days at a sucrose concentration of 55 g/l (Table 4).

TABLE 4

| | PEMs/ml PCV | | |
|---|---|---|---|
| Apparatus | Day 0 | Day 6 | Day 14 |
| Impeller (97%, 20 g/l sucrose) | 2300 | 800 | 40 |
| Vibromixer (97%, 20 g/l sucrose) | 2300 | 2300 | 2280 |
| Vibromixer (97%, 55 g/l sucrose) | 2300 | 6000 | 6000 |

EXAMPLE 16

Development of PEMs into Torpedo Stage Somatic Embryos in Bioreactors

2×100,000 sieved PEMs are collected from cucumber PEM suspension cultures subcultured as described in Example 15 (55 g/l sucrose in vibromixer) and inoculated into 2 bioreactors (Applikon Dependable Instruments B. V.) comprising one conventional 2 l bioreactor fitted with impeller, and one bioreactor fitted with a vibromixer commercially available from Chemap AG, each containing 1 l MS medium containing 20 g/l sucrose, and ABA at a concentration of 5.0 μM. Oxygen is sparged into the vibromixer reactor via a 15 μm porous sparging device located at the end of the vibrator shaft positioned near the base of the reactor chamber. The oxygen concentration in the vibromixer reactor is determined at 97% following standard techniques known in the art. The vibromixer is operated at a frequency of 50 Hz and a maximum amplitude of ±6 mm. The vibromixer is positioned such that the vibrating motion is in the vertical plane and horizontal motion is kept to a minimum. The stirring disc is fitted on the end of the vibrating shaft such that fluid flows in a current loop drawing the PEMs from the periphery of the reactor vessel towards the base and then upwards.

Oxygen is sparged into the conventional bioreactor at the bottom of the bioreactor via a sparging tube fitted with a 15 μm porous sparger. Dissolved oxygen concentration is determined as per the above at a starting concentration of 97% and permitted to fall over 7 days to 30%±5%. At day 8 the dissolved oxygen concentration is reset at 97% and maintained at that level. Stirring speed of the impeller is maintained at about 190 rpm ±5 rpm.

The conventional bioreactor has a PEM to full grown, usable torpedo stage somatic embryo development efficiency of between 10–15%. The vibromixer bioreactor has a PEM to full grown usable, torpedo stage somatic embryo development efficiency greater than 20%. Usable torpedo stage somatic embryos are ones which give rise to normal looking plants.

EXAMPLE 17

Morphological stability of cyclamen plants derived from somatic embryos

Cyclamen somatic embryos obtained according to example 2 are converted into plantlets by placing the somatic embryos on potting soil. After formation of the first leaf plantlets are transferred to the greenhouse and grown to maturity. Plants are grown to the flowering stage. Morphological examination of flowering plants does not reveal abnormalities in the plants. No somaclonal variation due to genetic differences is observed in the plants.

EXAMPLE 18

Genetic somaclonal variation in cucumber plants derived from somatic embryos

Somatic embryos obtained according to example 6 are converted into plants on Sorbarod plugs (Baumgartner papier, Switzerland) and grown into fruit bearing plants. Ploidy level is determined by the method of De Laat A. M. M. et al supra, on 80 plants. All plants have the same ploidy level and differences due to genetic somaclonal variation are not observed.

EXAMPLE 19

Conversion of Cucumber Somatic Embryos into Plants

Cucumber PEMs are multiplied in bioreactors equipped with Vibromixers at low light intensities, sieved (100–150 µm) and inoculated in Erlenmeyer flasks at a density of 5000 PEMs/50 ml MS medium, supplemented with 20 g/l sucrose and 5 µM ABA. PEMs are split into two (2) batches which are further developed in the light and in the dark to somatic embryos.

Somatic embryos from both batches are converted into plants in the light. Results show that the conversion efficiency from somatic embryos into plants for somatic embryos derived from PEMs cultured in the dark is higher than for somatic embryos developed in the light (Table 5).

TABLE 5

| light condition | overall torpedo to plant conversion rate [%] |
|---|---|
| light | 28.6 |
| dark | 62.7 |

EXAMPLE 20

PEM aggregate size in relation to formation of single torpedos suitable for conversion to plants. 9 day old PEM suspension obtained as described in Example 5 above using medium supplemented with 10 mg/l 2,4-D and 0.5 mg/l kinetin (at a PEM concentration of 50 ml PCV/l ) is sieved on nylon meshes in three separate events to obtain three different sized PEM fractions: 100–150 µ, 150–200 µm, and 200 µm–250 µm. Embryo development is performed at initial PEM concentrations of about 25–50 PEMs/ml in MS medium containing 3 µM ABA. After 9 days of development culture the number of torpedo stage embryos is assessed under light microscopy. The number of single torpedos is assessed in relation to the number of multi-torpedos. The torpedo/PEM ratio is 5–15%. The fraction<100 µm in size does not contain PEMs. Results are shown in Table 6.

TABLE 6

| Sieve fraction size (µm) | % Single Torpedos as a percentage of total |
|---|---|
| 100–150 | 85 |
| 150–200 | 20 |
| 200–250 | 5 |

Single embryos are separated out from the 100–150 µm size fraction manually, and converted into single plants.

We claim:

1. A method of obtaining somatic embryos from non-callus material in suspension culture which comprises:
   (i) culturing non-Daucus non-callus explant material in a liquid medium comprising an effective amount of auxin or mixture of auxins sufficient to promote the induction of pro-embryogenic mass (PEM) formation;
   (ii) increasing the number of induced PEMs by cultivation of said PEMs in an auxin-containing liquid medium;
   (iii) collecting PEMs obtained in step (ii) and placing them in an auxin-free liquid medium to induce somatic embryo formation;
   (iv) inducing somatic embryo formation; and
   (v) collecting somatic embryos resulting from the induced embryos of step (iv)

wherein the somatic embryos collected in step (v) have the same ploidy level as the non-callus starting material in suspension culture and said ploidy level is either diploid or tetraploid.

2. The method according to claim 1, wherein the ploidy level is diploid.

3. The method according to claim 1, wherein the ploidy level is tetraploid.

4. The method according to claim 1, wherein the PEMs in step (iii) are about 1.0 mm or less in diameter.

5. The method according to claim 1, wherein the PEMs in step (iii) are about 0.5 mm or less in diameter.

6. The method according to claim 1, wherein at least about 5% of viable PEMs comprise the PEMs obtained in step (iii).

7. The method according to claim 1, wherein the liquid medium of step (i) further comprises a carbohydrate energy source at a concentration of between about 15 g/l and 90 g/l.

8. The method according to claim 7 wherein the carbohydrate energy source concentration lies between about 20 g/l and 60 g/l.

9. The method according to claim 8 wherein the carbohydrate source is selected from the group consisting of sucrose, glucose and raffinose.

10. The method according to claim 1 wherein the induced PEMs in an auxin containing liquid suspension are vibrated in a vibromixer.

11. The method according to claim 10 wherein the vibromixer is vibrated in the vertical plane wherein lateral or horizontal motion is kept to a minimum.

12. The method according to claim 1 wherein the explant material is derived from protoplasts, stem, leaf, petal, hypocotyl section, apical meristem,zygotic embryo, tuber, vascular bundle, pericycle, ovaries or anther filament.

13. The method according to claim 1 wherein the explant material is dicotyledonous.

14. The method according to claim 1 wherein the explant material is monocotyledonous.

\* \* \* \* \*